United States Patent
Noba et al.

(10) Patent No.: US 10,844,408 B2
(45) Date of Patent: Nov. 24, 2020

(54) METHOD FOR MANUFACTURING FUMARIC ACID

(71) Applicant: KAO CORPORATION, Tokyo (JP)

(72) Inventors: Masahiro Noba, Wakayama (JP); Shingo Koyama, Wakayama (JP)

(73) Assignee: KAO CORPORATION, Tokyo (JP)

( * ) Notice: Subject to any disclaimer, the term of this patent is extended or adjusted under 35 U.S.C. 154(b) by 39 days.

(21) Appl. No.: 16/065,497

(22) PCT Filed: Dec. 22, 2016

(86) PCT No.: PCT/JP2016/088277
§ 371 (c)(1),
(2) Date: Jun. 22, 2018

(87) PCT Pub. No.: WO2017/110963
PCT Pub. Date: Jun. 29, 2017

(65) Prior Publication Data
US 2019/0040423 A1 Feb. 7, 2019

(30) Foreign Application Priority Data

Dec. 24, 2015 (JP) ................................. 2015-251573

(51) Int. Cl.
*C12P 7/46* (2006.01)
*C07C 51/43* (2006.01)

(52) U.S. Cl.
CPC ................ *C12P 7/46* (2013.01); *C07C 51/43* (2013.01)

(58) Field of Classification Search
CPC .................................... C12P 7/46; C07C 51/43
See application file for complete search history.

(56) References Cited

U.S. PATENT DOCUMENTS

2015/0125915 A1  5/2015  Tsuboi et al.

FOREIGN PATENT DOCUMENTS

| JP | 2006-185911 A | 7/2006 |
|---|---|---|
| JP | 2006-230232 A | 9/2006 |
| JP | 2009-108194 A | 5/2009 |
| JP | 2013-236624 A | 11/2013 |
| JP | 2016-202073 A | 12/2016 |
| JP | 2018-43972 A | 3/2018 |
| WO | WO 2016/171215 A1 | 10/2016 |

OTHER PUBLICATIONS

CN103204772A, English translation 8 pages of PDF, publication date Jul. 17, 2013.*
Gangl et al., "Economic Comparison of Calcium Fumarate and Sodium Fumarate Production by *Rhizopus arrhizus*", Applied Biochemistry and Biotechnology, 1990, vol. 24/25, pp. 663-677.
Goldberg et al., "Improved Rate of Fumaric Acid Production by Tweens and Vegetable Oils in Rhizopus arrhizus", Biotechnology and Bioengineering, Jul. 1985, vol. 27, pp. 1067-1069.
International Search Report for PCT/JP2016/088277 dated Mar. 28, 2017.
Sasaki et al., "Organic Acid Fermentation Using the Genus *Rhizopus*", Journal of Fermentation Technology, 1967, vol. 45, No. 3, pp. 211-217.

* cited by examiner

*Primary Examiner* — Kade Ariani
(74) *Attorney, Agent, or Firm* — Birch, Stewart, Kolasch & Birch, LLP

(57) ABSTRACT

The present invention provides a novel method for manufacturing fumaric acid having favorable tone of color. A method for manufacturing fumaric acid, comprising the following steps (1) and (2): (1) a step of culturing a microorganism having fumaric acid-producing ability in a liquid culture medium comprising a carbon source to obtain one or more substances selected from fumaric acid and a fumarate, (2) a step of crystallizing the one or more substances selected from fumaric acid and a fumarate obtained in the step (1) in the presence of one or more surfactants selected from a nonionic surfactant and an amphoteric surfactant.

13 Claims, No Drawings

METHOD FOR MANUFACTURING FUMARIC ACID

FIELD OF THE INVENTION

The present invention relates to a method for manufacturing fumaric acid.

BACKGROUND OF THE INVENTION

Fumaric acid is utilized for, for example, a raw material of plastic such as an alkyd resin, food additive, bath agent and intermediate material for converting into commodity chemicals such as aspartic acid. Fumaric acid is manufactured industrially as petrochemicals made from benzene or butane. Recently, manufacturing fumaric acid using renewable resources is required from the viewpoint of depletion of fossil resources and an environmental issue such as global warming.

Examples of the known methods for manufacturing fumaric acid using renewable resources include a method for producing fumaric acid from glucose by culturing *Rhizopus* sp. (Non Patent Literature 1). Non Patent Literature 1 discloses a method of purifying fumaric acid by adding an acid to a culture medium containing a fumarate, filtrating and drying the resultant crystal of fumaric acid.

Non Patent Literature

Non Patent Literature 1: Appl. Biochem. Biotechnol., 1990, Vol. 24-25, p. 663-677

SUMMARY OF THE INVENTION

The present invention provides a method for manufacturing fumaric acid, comprising the following steps (1) and (2):

(1) a step of culturing a microorganism having fumaric acid-producing ability in a liquid culture medium comprising a carbon source to obtain one or more substances selected from the group consisting of fumaric acid and a fumarate, (2) a step of crystallizing the one or more substances selected from the group consisting of fumaric acid and a fumarate obtained in the step (1) in the presence of one or more surfactants selected from the group consisting of a nonionic surfactant and an amphoteric surfactant.

DETAILED DESCRIPTION OF THE INVENTION

For utilizing purified fumaric acid industrially, specifically as a food additive, less colored fumaric acid is required.

However, when fumaric acid is purified and manufactured by a method described in Non Patent Literature 1, a problem that the fumaric acid is colored has been revealed.

Generally, as a method for reducing coloration of a culture product, a method including treatment with activated carbon before a crystallization step is known. However, the present inventors revealed, as a result of consideration, that reduction of coloration of fumaric acid cannot be achieved by an activated carbon treatment at an industrially practicable level. On the other hand, it was found that although treatment with excess activated carbon can reduce coloration of fumaric acid, a recovery rate is considerably reduced by adsorption of fumaric acid onto the activated carbon, and thus an activated carbon treatment is not suitable as a means for reducing coloration of fumaric acid industrially.

Accordingly, the present invention relates to providing a novel method for manufacturing fumaric acid having favorable tone of color.

The present inventors, after pursuing a diligent study in view of the above problems, found that fumaric acid having favorable tone of color can be obtained by crystallizing one or more substances selected from the group consisting of fumaric acid and a fumarate obtained by a step of culturing a fungal cell in the presence of one or more surfactants selected from the group consisting of a nonionic surfactant and an amphoteric surfactant.

According to the method of the present invention, fumaric acid having favorable tone of color can be obtained by a convenient operation.

The method for manufacturing fumaric acid according to the present invention comprises: (1) a step of culturing a microorganism having fumaric acid-producing ability in a liquid culture medium containing a carbon source to obtain one or more substances selected from the group consisting of fumaric acid and a fumarate, and (2) a step of crystallizing the one or more substances selected from the group consisting of fumaric acid and a fumarate obtained in the step (1) in the presence of one or more surfactants selected from the group consisting of a nonionic surfactant and an amphoteric surfactant.

As used herein, "one or more substances selected from fumaric acid and a fumarate" is also referred to as "fumaric acid (salt)".

[Step (1)]

According to the method of the present invention, first, a microorganism having fumaric acid-producing ability is cultured in a liquid culture medium containing a carbon source to obtain one or more substances selected from fumaric acid and a fumarate.

(Liquid Culture Medium Containing Carbon Source)

The liquid culture medium as used herein can be any of a synthetic medium, a natural medium, or a semi-synthesized medium containing a synthetic medium supplemented with a natural ingredient.

Examples of the carbon source include saccharides. Examples of the saccharides include monosaccharides such as glucose, fructose, and xylose and disaccharides such as sucrose, lactose, and maltose. The saccharides can be an anhydride or a hydrate. Further, carbohydrate solution containing a saccharide, for example, a carbohydrate solution or molasses (blackstrap molasses) obtained from starch or a carbohydrate solution obtained from cellulosic biomass can also be used. Specifically, glucose and fructose are preferred in view of a high fumaric acid-producing ability by a microorganism.

The above carbon source can be used alone, or two or more of the carbon sources can be used in combination.

In view of a high fumaric acid-producing ability by a microorganism, the concentration of the carbon source in liquid culture medium is preferably 1% by mass or more, more preferably 2% by mass or more, still more preferably 3% by mass or more; and preferably 40% by mass or less, more preferably 30% by mass or less, still more preferably 20% by mass or less, still more preferably 10% by mass or less.

The liquid culture medium can contain, for example, a nitrogen source, inorganic salts, and other necessary nutrients in addition to the carbon source.

Examples of the nitrogen source include nitrogen-containing compounds such as ammonium sulfate, urea, ammonium nitrate, potassium nitrate, and sodium nitrate.

The concentration of the nitrogen source in the liquid culture medium is preferably 0.001% by mass or more, more preferably 0.05% by mass or more; and preferably 0.5% by mass or less, more preferably 0.2% by mass or less.

Examples of the inorganic salt include a sulfate, a magnesium salt, and a zinc salt. Examples of the sulfate include magnesium sulfate, zinc sulfate, potassium sulfate, and sodium sulfate. Examples of the magnesium salt include magnesium sulfate, magnesium nitrate, and magnesium chloride. Examples of the zinc salt include zinc sulfate, zinc nitrate, and zinc chloride.

The concentration of the sulfate in the liquid culture medium is preferably 0.01% by mass or more, more preferably 0.02% by mass or more; and preferably 0.5% by mass or less, more preferably 0.2% by mass or less.

The concentration of the magnesium salt in the liquid culture medium is preferably 0.001% by mass or more, more preferably 0.01% by mass or more; and preferably 0.5% by mass or less, more preferably 0.1% by mass or less.

The concentration of the zinc salt in the liquid culture medium is preferably 0.001% by mass or more, more preferably 0.005% by mass or more; and preferably 0.05% by mass or less, more preferably 0.02% by mass or less.

The pH of the liquid culture medium (at 25° C., the same applies hereinafter) is preferably 3 or more, more preferably 3.5 or more; and preferably 7 or less, more preferably 6 or less. The pH of the medium can be adjusted by using a buffer, as desired.

(Microorganism Having Fumaric Acid-Producing Ability)

Examples of the microorganism having fumaric acid-producing ability include a filamentous fungus, a colon bacillus, *Bacillus subtilis*, a yeast, and an actinomycete. Specifically, in view of handling and high fumaric acid-producing ability, a filamentous fungus is preferred.

Examples of the filamentous fungus include microorganisms belonging to *Rhizopus*, *Aspergillus*, and *Mucor*. A microorganism belonging to *Rhizopus* is preferred.

Examples of *Rhizopus* sp. include, but are not limited to, *Rhizopus delemar*, *Rhizopus oryzae*, *Rhizopus arrhizus*, *Rhizopus chinensis*, *Rhizopus nigricans*, *Rhizopus tonkinensis*, and *Rhizopus tritici*. The *Rhizopus* sp. can be used alone, or two or more of them can be used in combination.

The filamentous fungus, specifically *Rhizopus* sp. is preferably used in a form of a pellet, or in a form immobilized on a carrier. The term "pellet" of *Rhizopus* sp. refers to a mycelial mass having a size of several hundreds of micrometers to several millimeters formed autonomously by a mycelium due to liquid culture. The term "immobilized on a carrier" refers to a state retained by or embedded in a carrier. Commercially available pellet or pellet immobilized on a carrier can be used, and the pellet or the pellet immobilized on a carrier prepared by using a spore or a mycelium can also be used.

(Method of Culturing)

Fumaric acid production is carried out by culturing a microorganism having fumaric acid-producing ability in the above liquid culture medium. The microorganism can be cultured according to commonly used culture conditions. For example, the culture temperature is preferably 20° C. or more, more preferably 30° C. or more; and preferably 40° C. or less, more preferably 37° C. or less in view of growth of a fungal cell and a high fumaric acid-producing ability.

A conventionally known culture vessel can be appropriately used as a culturing vessel. However, in view of a high fumaric acid-producing ability, the vessel is preferably an aeration-agitation culture vessel, a bubble column culture vessel, and a fluidized-bed culture vessel. The culture can be batch culture, semi-batch culture, and continuous culture. The aeration condition is preferably 0.1 vvm or more, more preferably 0.2 vvm or more; and preferably 2 vvm or less, more preferably 1 vvm or less in view of a high fumaric acid-producing ability. The culture period can be appropriately adjusted.

When fumaric acid is produced, the pH of the culture medium is decreased by the produced fumaric acid. Thus, the culture is preferably carried out along with neutralization using a neutralizer.

Examples of the neutralizer used for pH control include a hydroxide of an alkali metal or an alkaline-earth metal, a carbonate of an alkali metal or an alkaline-earth metal, an ammonium compound, or a combination thereof. Specifically, in view of solubility of fumaric acid and in view of economy, the neutralizer is preferably sodium hydroxide, potassium hydroxide, calcium hydroxide, sodium carbonate, potassium carbonate, calcium carbonate, magnesium carbonate, ammonia water, ammonium carbonate, and ammonium bicarbonate; more preferably sodium hydroxide, sodium carbonate, and potassium carbonate; still more preferably sodium hydroxide. The neutralizer can be used alone, or two or more of the neutralizers can be used in combination.

The fumaric acid produced can form a salt with the neutralizer to provide a fumarate.

As a result of the culture, fumaric acid (salt) is accumulated in the medium.

With respect to the culture medium containing a fumaric acid (salt), when the culture is completed, an insoluble matter, such as a microorganism, is preferably removed from the culture by an appropriate separation means, for example, centrifugal separation or membrane treatment such as microfiltration. On the other hand, the microorganism such as *Rhizopus* sp. separated from the culture medium can be reused for the production of fumaric acid.

An amount of fumaric acid (salt) contained in the culture medium obtained in the step (1) is preferably 0.5% by mass or more, more preferably 1% by mass or more; and preferably 20% by mass or less, more preferably 10% by mass or less, still more preferably 3% by mass or less in view of a recovery rate and manufacturing cost.

[Step (2)]

Step (2) is a step of crystallizing the one or more substances selected from fumaric acid and fumarate obtained in the step (1) in the presence of one or more surfactants selected from a nonionic surfactant and an amphoteric surfactant.

The step (2) may be a step of crystallizing fumaric acid from the culture medium containing the one or more substances selected from fumaric acid and a fumarate obtained in the step (1) in the presence of one or more surfactants selected from a nonionic surfactant and an amphoteric surfactant. Alternatively, the step can be a step of separating the one or more substances selected from fumaric acid and a fumarate obtained in the step (1) from the culture medium, and then crystallizing fumaric acid again from the aqueous solution containing the one or more substances selected from fumaric acid and a fumarate in the presence of one or more surfactants selected from a nonionic surfactant and an amphoteric surfactant.

In the step (2), when the one or more surfactants selected from a nonionic surfactant and an amphoteric surfactant are added directly to the culture medium containing fumaric acid (salt) to crystallize fumaric acid, the step is simplified and advantageous in cost. Further, when a fumaric acid (salt) is separated from the culture medium and then the aqueous solution containing the separated fumaric acid (salt) is added with one or more surfactants selected from a nonionic surfactant and an amphoteric surfactant to crystallize fumaric acid, the fumaric acid can be crystallized along with less contaminants, and thus the degree of purification can easily be increased.

In the present invention, the step (2) is preferably a step of crystallizing fumaric acid from the culture medium containing the one or more substances selected from fumaric acid and a fumarate obtained in the step (1) in the presence of one or more surfactants selected from a nonionic surfactant and an amphoteric surfactant.

(Surfactant)

The surfactants used in the present invention are one or more surfactants selected from a nonionic surfactant and an amphoteric surfactant. The surfactant can be used alone, or a plurality of the surfactants can be used in combination. When a plurality of the surfactants are used in combination, the nonionic surfactant and the amphoteric surfactant can be used in combination. Further, a plurality of the nonionic surfactants can be used in combination, or a plurality of the amphoteric surfactants can be used in combination.

Timing of addition of the surfactant to the culture medium or the aqueous solution containing fumaric acid (salt) is not specifically limited. The surfactant can be added at any timing as long as the surfactant is present at the time of crystallization of the fumaric acid.

(Nonionic Surfactant)

Examples of the nonionic surfactant used in the present invention include glycerin fatty acid ester, propylene glycol fatty acid ester, sorbitan fatty acid ester, polyoxyethylene sorbitan fatty acid ester, sucrose fatty acid ester, polyoxyethylene sorbitol fatty acid ester, polyoxyethylene alkyl ether, polyoxyethylene alkenyl ether, polyoxyethylene polyoxypropylene glycol, polyoxyethylene polyoxypropylene alkyl ether, polyoxyethylene polyoxypropylene alkenyl ether, polyethylene glycol fatty acid ester, polyoxyethylene castor oil, polyoxyethylene hydrogenated castor oil, and polyglycerol fatty acid ester.

When a nonionic surfactant having an ethylene oxide (EO) chain is used, the number of moles of ethylene oxide added is preferably 4 or more, more preferably 5 or more, still more preferably 6 or more; and preferably 250 or less, more preferably 160 or less, still more preferably 80 or less, still more preferably 60 or less, still more preferably 50 or less, still more preferably 25 or less, still more preferably 18 or less. The number of carbons of the fatty acid moiety, the alkyl moiety, the alkylene moiety, and the alkenyl moiety of the nonionic surfactant is preferably 6 or more, more preferably 8 or more, still more preferably 10 or more; and preferably 24 or less, more preferably 22 or less, still more preferably 20 or less.

In view of providing an effect of removing coloring components, types of the nonionic surfactant is preferably polyoxyethylene alkyl ether, polyoxyethylene sorbitan fatty acid ester, polyoxyethylene hydrogenated castor oil, polyoxyethylene sorbitol fatty acid ester, and polyoxyethylene polyoxypropylene alkyl ether; more preferably polyoxyethylene alkyl ether, and polyoxyethylene sorbitan fatty acid ester.

The HLB (Hydrophilic-Lipophilic Balance) of the nonionic surfactant is more preferably 10 or more, still more preferably 12 or more; and preferably 20 or less, more preferably 19 or less, still more preferably 17 or less in view of providing an effect of removing coloring components, preferably 6 or more.

In the present invention, HLB can be calculated from an inorganic value and an organic value obtained according to ODA and TERAMURA et. al.

The HLB calculated from the inorganic value and the organic value can be specifically calculated by the following equation: HLB=($\Sigma$ inorganic value/$\Sigma$ organic value)×10. With respect to the "inorganic value" and the "organic value", "inorganic values" and "organic values" corresponding to various atoms or functional groups are defined (e.g., see Yoshio KODA (1984). Yuki Gainenzu—Kiso to Oyo (Organicity Chart—Basics and Applications), 11-17, SANKYO SHUPPAN Co., Ltd.). For example, an "organic value" of one carbon atom in a molecule is 20, and an "inorganic value" of one hydroxyl group in a molecule is 100. The HLB of a certain organic compound can be calculated by addition of "inorganic values" and "organic values" of all atoms and functional groups in the organic compound.

Further, when a composition of surfactants comprises two or more nonionic surfactants, the HLB of the composition is an arithmetic mean of HLB values of each of the nonionic surfactants on the basis of their mass ratios in the composition according to the following equation.

$$\text{HLB of composition} = \Sigma(\text{HLB}x \times Wx)/\Sigma Wx$$

In the formula, HLBx represents HLB value of a nonionic surfactant X, and Wx represents mass (g) of the nonionic surfactant X having the value of HLBx.

(Amphoteric Surfactant)

Examples of the amphoteric surfactant include an amidobetaine surfactant, an amide amino acid surfactant; an alkyl betaine surfactant, a sulfobetaine surfactant, an imidazolinium betaine surfactant, and a phosphobetaine surfactant. Specifically; in view of providing an effect of removing coloring components, an alkyl betaine surfactant and a sulfobetaine surfactant are preferred, and alkyldimethylamino acetic acid betaine is more preferred. The number of carbons of the alkyl moiety of the alkyl betaine surfactant is preferably 6 or more, more preferably 8 or more, still more preferably 10 or more; and preferably 22 or less, more preferably 20 or less, still more preferably 18 or less in view of providing an effect of: removing coloring components.

In the present invention, in view of providing an effect of removing coloring components, one or more surfactants selected from nonionic surfactants are preferably used. The HLB of the nonionic surfactant when the surfactant is used alone, and the arithmetic mean of HLBs of two or more nonionic surfactants when the two or more surfactants are used, are preferably 10 or more, more preferably 12 or more; and preferably 20 or less, more preferably 17 or less.

Commercially available nonionic surfactants and amphoteric surfactants can be used.

(Concentration of Surfactant)

An amount of a surfactant used in crystallization of fumaric acid is not specifically limited. However, in view of a removal rate of coloring components, the amount is preferably 0.0001 or more, and in view of industrial productivity and cost, the amount is preferably 1 or less relative to fumaric acid (salt).

Further, from the same viewpoint, the total concentration of surfactants in crystallization of fumaric acid is preferably 0.0001% by mass or more, more preferably 0.001% by mass or more, still more preferably 0.01% by mass or more; and preferably 5% by mass or less, more preferably 2% by mass or less, still more preferably 1% by mass or less in the culture, medium or an aqueous solution containing fumaric acid (salt).

(Method for Crystallizing Fumaric Acid)

A method for crystallizing fumaric acid is not specifically limited. Fumaric acid can be crystallized through pH control, cooling, and concentration.

Crystallization of fumaric acid is preferably carried out using a reactor equipped with an agitator blade with stirring. The agitator blade can have any shape. Specifically, in order to mix crystals efficiently, the agitator blade is preferably a paddle blade, a turbine blade, a propeller blade, an anchor blade, a large diameter paddle blade, and a Max Blend blade. Following description is an example of crystallizing fumaric acid from the culture medium containing fumaric acid (salt).

In crystallization by pH control, as a result of dissociation of fumarate into fumaric acid and a salt, the fumaric acid concentration is increased to equal to or higher than the solubility of fumaric acid, and thus fumaric acid can be crystallized.

An acid used for pH control of the culture medium is not specifically limited, as long as the acid is an inorganic acid with a pKa lower than that of fumaric acid. Examples of the inorganic acid include hydrochloric acid, nitric acid, sulfuric acid, and phosphoric acid. The inorganic acid is preferably sulfuric acid and hydrochloric acid. An amount of the inorganic acid added can be appropriately adjusted according to the pH of the culture medium containing fumaric acid (salt) obtained in the step (1).

In view of a fumaric acid recovery rate, the pH of the medium is adjusted to preferably 3.5 or less, more preferably 3 or less, still more preferably 2.5 or less. Further, in view of causticity, the pH is preferably 0.5 or more, more preferably 1 or more.

The temperature when fumaric acid is crystallized by pH control is not specifically limited. However, in view of the fumaric acid recovery rate, it is preferred to carry out the crystallization after cooling of the culture medium.

In view of the fumaric acid recovery rate, the temperature of the cooling is preferably 35° C. or less, more preferably 30° C. or less, still more preferably 25° C. or less; and preferably 0° C. or more, more preferably 4° C. or more.

In view of productivity, the rate of addition of an acid is preferably 0.1 [mmol acid/L of culture medium/min] or more, more preferably 0.3 [mmol acid/L of culture medium/min] or more; and in view of purity, preferably 20 [mmol acid/L of culture medium/min] or less, more preferably 10 [mmol acid/L of culture medium/min] or less, still more preferably 5 [mmol acid/L of culture medium/min] or less, still more preferably 3 [mmol acid/L of culture medium/min] or less.

In crystallization by cooling, as a result of cooling of the culture medium containing fumaric acid, the fumaric acid concentration can be increased to equal to or higher than the solubility of fumaric acid, and thus fumaric acid can be crystallized.

For homogeneous crystallization of fumaric acid, the cooling can be carried out after heating. Further, the culture medium can be concentrated, then heated, and then cooled. Further, in view of purity, the culture medium can be heated, and the above acid can be added to the culture medium before cooling to adjust the pH within the range described above. The temperature of heating is preferably 40° C. or more, more preferably 55° C. or more; and preferably 100° C. or less.

In view of the fumaric acid recovery rate, the temperature of the cooling is preferably 35° C. or less, more preferably 30° C. or less, still more preferably 25° C. or less; and preferably 0° C. or more, more preferably 4° C. or more.

The rate of cooling calculated based on the time required for reaching the temperature of cooling as starting from the culture temperature or the temperature of heating is preferably 0.05 [° C./min] or more, more preferably 0.1 [° C./min] or more, still more preferably 0.2 [° C./min] in view of productivity and purity; and preferably 10 [° C./min] or less, more preferably 5 [° C./min] or less in view of purity.

In crystallization by concentration, as a result of concentration of the culture medium containing fumaric acid, the fumaric acid concentration can be increased to equal to or higher than solubility of fumaric acid, and thus fumaric acid can be crystallized.

In view of the fumaric acid recovery rate, before crystallization by concentration, the above acid can be added to the culture medium to adjust the pH within the range described above.

These methods for crystallization can be carried out alone, or two or more of the methods can be carried out in combination. when two or more of the methods are carried out in combination, crystallization by pH control, and crystallization by cooling and/or crystallization by concentration are preferably carried out in view of the fumaric acid recovery rate.

In the present invention, as a method for crystallizing fumaric acid, in view of obtaining high-purify fumaric acid and in view of the fumaric acid recovery rate, the method preferably includes heating the culture medium containing fumaric acid (salt), then adjusting the pH, and then crystallizing fumaric acid by cooling. Specifically, the method preferably includes heating the culture medium containing fumaric acid (salt) to 55° C. or more, then adding an acid to make the pH 3 or less, and then cooling to 25° C. or less to crystallize fumaric acid.

Further, as a method for crystallizing fumaric acid, in view of obtaining purified fumaric acid economically, the method preferably includes cooling the culture medium containing fumaric acid (salt), and then crystallizing fumaric acid by pH control. Specifically, the method preferably includes cooling the culture medium containing fumaric acid (salt) to 25° C. or less, and then adding an acid to make the pH 3 or less to crystallize fumaric acid.

In any of the methods for crystallization, in view of the fumaric acid recovery rate, the temperature of cooling of the culture medium at completion of the crystallization is preferably 35° C. or less, more preferably 30° C. or less, still more preferably 25° C. or less, still more preferably 20° C. or less; and preferably 0° C. or more, more preferably 4° C. or more in view of the fumaric acid recovery rate.

Further, the pH of the culture medium at completion of crystallization is adjusted to preferably 3.5 or less, more preferably 3 or less, still more preferably 2.5 or less in view of the fumaric acid recovery rate; and preferably 0.5 or more, more preferably 1 or more in view of causticity.

A crystal of fumaric acid can be isolated by solid-liquid separation methods such as centrifugal separation, filtration, and decantation. Operations such as the separation operation of a crystal is preferably carried out at a temperature within the range described above.

The crystal of fumaric acid obtained as described above is washed as required, and dried to obtain purified fumaric acid.

A drying method is not specifically limited. Drying can be carried out by using a conventional dryer such as a shelf type dryer, a paddle dryer, Nauta Mixer, a fluidized-bed dryer, a vacuum mixing dryer, and a disc dryer.

The temperature of drying is preferably 80° C. or more, more preferably 90° C. or more, still more preferably 100° C. or more; and preferably 150° C. or less, more preferably 130° C. or less, still more preferably 120° C. or less. The drying can be carried out under reduced pressure.

Fumaric acid obtained by a method of the present invention has a fine tone of color. The absorbance at a wavelength of 400 nm measured by the method described in the following Examples is preferably 0.02 or less, more preferably 0.015 or less.

The fumaric acid with a fine tone of color can be used as, for example, a raw material of plastics, a food additive, a bath agent, and an intermediate material for converting into commodity chemicals, such as aspartic acid. Specifically, the fumaric acid with fine tone of color is useful as a food additive.

With respect to the above described embodiments, the present invention also discloses the following manufacturing methods.

<1> A method for manufacturing fumaric acid, comprising the following steps (1) and (2):

(1) a step of culturing a microorganism having fumaric acid-producing ability in a liquid culture medium comprising a carbon source to obtain one or more substances selected from the group consisting of fumaric acid and a fumarate, (2) a step of crystallizing the one or more substances selected from the group consisting of fumaric acid and a fumarate obtained in the step (1) in the presence of one or more surfactants selected from the group consisting of a nonionic surfactant and an amphoteric surfactant.

<2> The method for manufacturing fumaric acid according to <1>, wherein the carbon source is preferably saccharides, more preferably glucose or fructose, still more preferably glucose.

<3> The method for manufacturing fumaric acid according to <1> or <2>, wherein the microorganism having fumaric acid-producing ability is preferably a filamentous fungus, a colon *bacillus, Bacillus subtilis*, a yeast, or an actinomycete, more preferably a filamentous fungus.

<4> The method for manufacturing fumaric acid according to <3>, wherein the filamentous fungus is preferably a microorganism belonging to *Rhizopus, Aspergillus*, or *Mucor*, more preferably a microorganism belonging to *Rhizopus*.

<5> The method for manufacturing fumaric acid according to <4>, wherein the microorganism belonging to *Rhizopus* is preferably *Rhizopus delemar, Rhizopus oryzae, Rhizopus arrhizus, Rhizopus chinensis, Rhizopus nigricans, Rhizopus tonkinensis*, or *Rhizopus tritici*.

<6> The method for manufacturing fumaric acid according to any one of <1> to <5>, wherein culture of the microorganism having fumaric acid-producing ability is carried out under an aeration condition of preferably 0.1 vvm or more, more preferably 0.2 vvm or more; and preferably 2 vvm or less, more preferably 1 vvm or less; at a temperature of preferably 20° C. or more, more preferably 30° C. or more; and preferably 40° C. or less, more preferably 37° C. or less.

<7> The method for manufacturing fumaric acid according to any one of <1> to <6>, wherein the culture of the microorganism having fumaric acid-producing ability is preferably carried out along with neutralization using a neutralizer.

<8> The method for manufacturing fumaric acid according to <7>, wherein the neutralizer is preferably a hydroxide of an alkali metal or an alkaline-earth metal, a carbonate of an alkali metal or an alkaline-earth metal, an ammonium compound, and a mixture thereof; more preferably one or more neutralizers selected from sodium hydroxide, potassium hydroxide, calcium hydroxide, sodium carbonate, potassium carbonate, calcium carbonate, magnesium carbonate, ammonia water, ammonium carbonate, and ammonium bicarbonate; still more preferably one or more neutralizers selected from sodium hydroxide, sodium carbonate, and potassium carbonate; still more preferably sodium hydroxide.

<9> The method for manufacturing fumaric acid according to any one of <1> to <8>, wherein an amount of the one or more substances selected from fumaric acid and a fumarate in the culture medium obtained in the step (1) is preferably 0.5% by mass or more, more preferably 1% by mass or more; and preferably 20% by mass or less, more preferably 10% by mass or less, still more preferably 3% by mass or less.

<10> The method for manufacturing fumaric acid according to any one of <1> to <9>, wherein the nonionic surfactant is preferably one or more surfactants selected from glycerin fatty acid ester, propylene glycol fatty acid ester, sorbitan fatty acid ester, polyoxyethylene sorbitan fatty acid ester, sucrose fatty acid ester, polyoxyethylene sorbitol fatty acid ester, polyoxyethylene alkyl ether, polyoxyethylene alkenyl ether, polyoxyethylene polyoxypropylene glycol, polyoxyethylene polyoxypropylene alkyl ether, polyoxyethylene polyoxypropylene alkenyl ether, polyethylene glycol fatty acid ester, polyoxyethylene castor oil, polyoxyethylene hydrogenated castor oil, and polyglycerol fatty acid ester; more preferably one or more surfactants selected from polyoxyethylene alkyl ether, polyoxyethylene sorbitan fatty acid ester, polyoxyethylene hydrogenated castor oil, polyoxyethylene sorbitol fatty acid ester, and polyoxyethylene polyoxypropylene alkyl ether; and still more preferably one or more surfactants selected from polyoxyethylene alkyl ether, polyoxyethylene sorbitan fatty acid ester.

<11> The method for manufacturing fumaric acid according to any one of <1> to <10>, wherein HLB of the nonionic surfactant is preferably 6 or more, more preferably 10 or more, still more preferably 12 or more; preferably 20 or less, more preferably 19 or less, still more preferably 17 or less; and preferably from 6 to 20, more preferably from 10 to 19, and still more preferably from 12 to 17.

<12> The method for manufacturing fumaric acid according to any one of <1> to <11>, wherein the amphoteric surfactant is preferably one or more surfactants selected from an amidobetaine surfactant, an amide amino acid surfactant, an alkyl betaine surfactant, a sulfobetaine surfactant, an imidazolinium betaine surfactant, and a phosphobetaine surfactant; more preferably one or more surfactants selected from an alkyl betaine surfactant, and a sulfobetaine surfactant; still more preferably alkyldimethylamino acetic acid betaine.

<13> The method for manufacturing fumaric acid according to any one of <1> to <12>, wherein the surfactant is preferably a nonionic surfactant, more preferably a nonionic surfactant with HLB of 12 or more.

<14> The method for manufacturing fumaric acid according to any one of <1> to <13>, wherein the step (2) is preferably a step of crystallizing fumaric acid from the culture medium containing one or more substances selected from fumaric acid and a fumarate obtained in the step (1) in the presence of one or more surfactants selected from a nonionic surfactant and an amphoteric surfactant, or a step of separating one or more substances selected from fumaric acid and fumarate obtained in the step (1) from the culture medium, and then crystallizing fumaric acid again from the aqueous solution containing one or more substances selected from fumaric acid and a fumarate in the presence of one or more surfactants selected from a nonionic surfactant and an amphoteric surfactant; more preferably a step of crystallizing fumaric acid from the culture medium containing one or more substances selected from fumaric acid and a fumarate obtained in the step (1) in the presence of one or more surfactants selected from a nonionic surfactant and an amphoteric surfactant.

<15> The method for manufacturing fumaric acid according to any one of <1> to <14>, wherein an amount of the surfactant used is preferably 0.0001 or more, and preferably 1 or less relative to the one or more substances selected from fumaric acid and a fumarate.

<16> The method for manufacturing fumaric acid according to any one of <1> to <14>, wherein a total concentration of surfactants in the culture medium or the aqueous solution containing one or more substances selected from fumaric acid and a fumarate is preferably 0.0001% by mass or more, more preferably 0.001% by mass or more, still more preferably 0.01% by mass or more; preferably 5% by mass or less, more preferably 2% by mass or less, still more preferably 1% by mass or less; and preferably from 0.0001 to 5% by mass, more preferably from 0.001 to 2% by mass, still more preferably from 0.01 to 1% by mass.

<17> The method for manufacturing fumaric acid according to any one of <1> to <16>, wherein the method for crystallizing fumaric acid is preferably one or more methods selected from crystallization by pH control, crystallization by cooling, and crystallization by concentration.

<18> The method for manufacturing fumaric acid according to <17>, wherein an acid used for the crystallization by pH control is preferably an inorganic acid with a pKa lower than that of fumaric acid, more preferably hydrochloric acid, nitric acid, sulfuric acid, or phosphoric acid, still more preferably sulfuric acid or hydrochloric acid.

<19> The method for manufacturing fumaric acid according to <18>, wherein a rate of addition of the acid is preferably 0.1 [mmol acid/L of culture medium/min] or more, more preferably 0.3 [mmol acid/L of culture medium/min] or more; and preferably 20 [mmol acid/L of culture medium/min] or less, more preferably 10 [mmol acid/L of culture medium/min] or less, more preferably 5 [mmol acid/L of culture medium/min] or less, still more preferably 3 [mmol acid/L of culture medium/min] or less.

<20> The method for manufacturing fumaric acid according to any one of <17> to <19>, wherein the crystallization by pH control is carried out by adjusting the pH to preferably 3.5 or less, more preferably 3 or less, still more preferably 2.5 or less; and preferably 0.5 or more, more preferably 1 or more.

<21> The method for manufacturing fumaric acid according to any one of <17> to <20>, wherein the crystallization by pH control is carried out preferably after cooling the culture medium; and the crystallization is carried out after cooling the culture medium to more preferably 35° C. or less, more preferably 30° C. or less, still more preferably 25° C. or less; and also preferably 0° C. or more, more preferably 4° C. or more as well.

<22> The method for manufacturing fumaric acid according to any one of <17> to <21>, wherein the crystallization by pH control is carried out by preferably cooling the culture medium to 25° C. or less, and then adding an acid to adjust the pH to 3 or less.

<23> The method for manufacturing fumaric acid according to <17>, wherein the crystallization by cooling is carried out preferably after heating the culture medium; and the crystallization is carried out after heating the culture medium to more preferably 40° C. or more, more preferably 55° C. or more; and also preferably 100° C. or less.

<24> The method for manufacturing fumaric acid according to <17> or <23>, wherein the crystallization by cooling is carried out preferably after heating the culture medium, and subsequently adding an acid to adjust the pH to preferably 3.5 or less, more preferably 3 or less, still more preferably 2.5 or less; and also preferably 0.5 or more, more preferably 1 or more.

<25> The method for manufacturing fumaric acid according to <17>, <23>, or <24>, wherein the crystallization by cooling is carried out by cooling the culture medium to preferably 35° C. or less, more preferably 30° C. or less, still more preferably 25° C. or less; and also preferably 0° C. or more, more preferably 4° C. or more.

<26> The method for manufacturing fumaric acid according to any one of <17>, and <23> to <25>, wherein a cooling rate calculated based on the time required for reaching the temperature of cooling as starting from the culture temperature or the temperature of heating is preferably 0.05 [° C./min] or more, more preferably 0.1 [° C./min] or more, still more preferably 0.2 [° C./min] or more; and preferably 10 [° C./min] or less, more preferably 5 [° C./min] or less.

<27> The method for manufacturing fumaric acid according to any one of <17>, and <23> to <26>, wherein the crystallization by cooling is carried out by preferably heating the culture medium to 55° C. or more, then adding an acid to make the pH 3 or less, and then cooling to 25° C. or less.

<28> The method for manufacturing fumaric acid according to <17>, wherein the crystallization by concentration is carried out after preferably adding an acid to the culture medium to adjust the pH to preferably 3.5 or less, more preferably 3 or less, and still more preferably 2.5 or less; and also preferably 0.5 or more, and more preferably 1 or more.

<29> The method for manufacturing fumaric acid according to any one of <1> to <28>, wherein a temperature of cooling of the culture medium at completion of the fumaric acid crystallization is preferably 35° C. or less, more preferably 30° C. or less, still more preferably 25° C. or less, still more preferably 20° C. or less; and also preferably 0° C. or more, more preferably 4° C. or more.

<30> The method for manufacturing fumaric acid according to any one of <1> to <29>, wherein the pH of the culture medium at completion of the fumaric acid crystallization is preferably 3.5 or less, more preferably 3 or less, still more preferably 2.5 or less; and also preferably 0.5 or more, more preferably 1 or more.

<31> The method for manufacturing fumaric acid according to any one of <1> to <30>, wherein an absorbance of fumaric acid obtained by the method of the present invention at a wavelength of 400 nm measured by a method described in Examples herein is preferably 0.02 or less, more preferably 0.015 or less.

EXAMPLES

[*Rhizopus* sp.]

A bacterial strain used was a filamentous fungus *Rhizopus delemar* JCM5557 obtained from an Incorporated Administrative Agency of National Institute of Technology and Evaluation (NITE).

[Surfactant]

Surfactants used were as follows.

(Nonionic Surfactant)

Polyoxyethylene (6) lauryl ether: EMULGEN (registered trademark) 108, having a HLB calculated from inorganic value and organic value of 10.3 (HLB given in catalogue: 12.1), manufactured by Kao Corporation Polyoxyethylene (12) lauryl ether: EMULGEN 120, having HLB calculated from inorganic value and organic value of 13.1 (HLB given in catalogue: 15.3), manufactured by Kao Corporation Polyoxyethylene (47) lauryl ether: EMULGEN 150, having HLB calculated from inorganic value and organic value of 16.8 (HLB given in catalogue: 18.4), manufactured by Kao Corporation Polyoxyethylene (20) sorbitan monolaurate, having HLB calculated from inorganic value and organic value of 14.9 (HLB given in catalogue: 16.7), manufactured by Wako Pure Chemical Industries, Ltd.

Polyoxyethylene (20) sorbitan monooleate, having HLB calculated from inorganic value and organic value of 13.5 (HLB given in catalogue: 15.0), manufactured by Wako Pure Chemical Industries, Ltd.

Polyoxyethylene polyoxypropylene (C12-C14) alkyl ether: EMULGEN LS-114, having HLB calculated from inorganic value and organic value of 14, manufactured by Kao Corporation Polyoxyethylene (60) hydrogenated castor oil: EMANON CH-60(K), having HLB calculated from inorganic value and organic value of 13.6, manufactured by Kao Corporation Polyoxyethylene (60) sorbitol tetraoleate: RHEODOL 460V, having HLB calculated from inorganic value and organic value of 11.7, manufactured by Kao Corporation. The number in the parenthesis represents an average number of moles of EO added.

(Amphoteric Surfactant)

Lauryldimethylamino acetic acid betaine: AMPHITOL 20BS, manufactured by Kao Corporation 3-[(3-Cholamidopropyl)dimethylammonio]-1-propanesulfonate: CHAPS, manufactured by DOJINDO LABORATORIES (Anionic Surfactant)

Sodium lauryl sulfate: EMAL 0, manufactured by Kao Corporation (Comparative Example)

(Cationic Surfactant)

Hexadecyltrimethylammonium bromide, manufactured by Wako Pure Chemical Industries, Ltd. (Comparative Example)

[Evaluation of Tone of Color]

To 0.2 g of dried fumaric acid, 4 mL of 1 mol/L NaOH was added to dissolve the fumaric acid, and then the absorbance at a wavelength of 400 nm was measured using a quartz cell with an optical path length of 1 cm (ultraviolet and visible spectrophotometer UV-1800, manufactured by SHIMADZU CORPORATION). When the absorbance was smaller, the result was evaluated as favorable in tone of color.

Example 1

(1) Obtaining Culture Medium

To 15 L of liquid culture medium (4% by mass of glucose, 0.025% by mass of magnesium sulfate heptahydrate, 0.009% by mass of zinc sulfate heptahydrate, 0.1% by mass of ammonium sulfate), *Rhizopus* sp. was inoculated, and aeration-agitation culture was carried out for 12 hours under conditions of pH 4, temperature of the medium of 35° C., stirring speed of 200 r/min (agitator blade: ½ disc-turbine blade), and aeration of 0.6 vvm. During the culture, the pH was adjusted to 4 using aqueous sodium hydroxide.

When the culture was completed, fungal cells were removed by filtering the culture medium using a membrane filter system with pore size of 0.2 μm to obtain a culture medium containing 2.23% by mass of fumaric acid or its salts. The pH of the culture medium was 4.0.

(2) Crystallization of Fumaric Acid

Crystallization of fumaric acid was carried out in a jacket reactor (diameter of the reactor: 7.5 cm) having an internal volume of 600 mL equipped with an anchor blade having a blade diameter of 7 cm with stirring speed of 200 r/min.

First, 450 g of the culture medium obtained in (1) described above was heated to 60° C. Then, 0.45 g of EMULGEN 108 was added, and then sulfuric acid was added to adjust the pH to 2.2. Then, the culture medium was cooled to 5° C. at a cooling rate of 0.6° C./min to crystallize fumaric acid. Then the fumaric acid suspension in which fumaric acid was crystallized was filtered with suction using a No. 2 filter paper (MANUFACTURED BY ADVANTECH CO., LTD., the same applies hereinafter), and then 200 g of ion exchanged water was added for filtration washing. A cake of fumaric acid after the filtration was dried at 105° C. to obtain fumaric acid. The absorbance of the purified fumaric acid at 400 nm was 0.015.

Example 2 to 17

Fumaric acid was obtained in the same manner as Example 1, except that types and concentration of surfactants, pH, stirring speed, cooling rate, and temperature of cooling were modified as shown in Table 1. Further, the absorbance of purified fumaric acid at 400 nm was also as shown in Table 1.

Example 18

Crystallization of fumaric acid was carried out in a jacket reactor (diameter of the reactor: 7.5 cm) having an internal volume of 600 mL equipped with an anchor blade having a blade diameter of 7 cm with stirring speed of 200 r/min.

First, 450 g of the culture medium obtained in Example 1(1) described above was heated to 60° C., and then sulfuric acid was added to adjust the pH to 2.0. Then, the culture medium was cooled to 5° C. at a cooling rate of 0.6° C./min to crystallize fumaric acid. Then the fumaric acid suspension in which fumaric acid was crystallized was filtered with suction using a No. 2 filter paper (MANUFACTURED BY ADVANTECH CO., LTD., the same applies hereinafter), and then 200 g of ion exchanged water was added for filtration washing. A cake of fumaric acid after the filtration was dried at 105° C. to obtain fumaric acid. The absorbance of the fumaric acid at 400 nm was 0.026.

To ion exchanged water, the fumaric acid described above was added to make up to 300 g, then poured into a jacket reactor (diameter of the reactor: 7.5 cm) having an internal volume of 600 mL equipped with an anchor blade having a blade diameter of 7 cm, and stirred at stirring speed of 200 r/min. The mixture was heated to 60° C. Then, 0.45 g of EMULGEN 108 was added. Then, the fumaric acid aqueous solution was cooled to 5° C. at a cooling rate of 0.6° C./min to crystallize fumaric acid. Then, the fumaric acid suspension was filtered with suction using a No. 2 filter paper (MANUFACTURED BY ADVANTECH CO., LTD., the same applies hereinafter). A cake of the fumaric acid after the filtration was dried at 105° C. to obtain a colorless fumaric acid crystal.

Comparative Example 1

Crystallization of fumaric acid was carried out in a jacket reactor (diameter of the reactor: 7.5 cm) having an internal volume of 600 mL equipped with an anchor blade having a blade diameter of 7 cm with stirring speed of 200 r/min.

First, 450 g of the culture medium obtained in Example 1(1) described above was heated to 60° C., and then sulfuric acid was added to adjust the pH to 2.0. Then, the culture medium was cooled to 5° C. at a cooling rate of 0.6° C./min to crystallize fumaric acid. Then the fumaric acid suspension in which fumaric acid was crystallized was filtered with suction using a No. 2 filter paper (MANUFACTURED BY ADVANTECH CO., LTD., the same applies hereinafter), and then 200 g of ion exchanged water was added for filtration washing. A cake of fumaric acid after the filtration was dried at 105° C. to obtain fumaric acid. The absorbance of the purified fumaric acid at 400 nm was 0.026.

Comparative Example 2

To 500 g of the culture medium obtained in Example 1(1) described above, 0.5 g of activated carbon (granular SHIRASAGI WH2C8/32, manufactured by Japan Enviro-Chemicals, Ltd.) was added to perform an adsorption treatment. The activated carbon treatment was carried out by shake mixing at 100 r/min at 25° C. for 24 hours. After the adsorption treatment, the activated carbon was removed by filtering the culture medium using a membrane filter system with pore size of 0.2 μm. Then, the concentration of fumaric acid or its salts was 2.216 by mass.

Crystallization of fumaric acid was carried out in a jacket reactor (diameter of the reactor: 7.5 cm) having an internal volume of 600 mL equipped with an anchor blade having a blade diameter of 7 cm with stirring speed of 200 r/min.

First, 450 g of the culture medium treated with activated carbon was heated to 60° C., and then sulfuric acid was added to adjust the pH to 2.2. Then, the culture medium was cooled to 5° C. at a cooling rate of 0.6° C./min to crystallize fumaric acid. Then the fumaric acid suspension in which fumaric acid was crystallized was filtered with suction using a No. 2 filter paper (MANUFACTURED BY ADVANTECH CO., LTD., the same applies hereinafter), and then 200 g of ion exchanged water was added for filtration washing. A cake of fumaric acid after the filtration was dried at 105° C. to obtain fumaric acid. The absorbance of the purified fumaric acid at 400 nm was 0.021.

Comparative Example 3

Crystallization of fumaric acid was carried out in a jacket reactor (diameter of the reactor: 7.5 cm) having an internal volume of 600 mL equipped with an anchor blade having a blade diameter of 7 cm with stirring speed of 200 r/min.

First, 450 g of the culture medium obtained in Example 1(1) described above was heated to 60° C. Then, 0.45 g of EMAL 0 was added, and sulfuric acid was added to adjust the pH to 2.1. Then, the culture medium was cooled to 5° C. at a cooling rate of 0.6° C./min to crystallize fumaric acid. Then the fumaric acid suspension in which fumaric acid was crystallized was filtered with suction using a No. 2 filter paper (MANUFACTURED BY ADVANTECH CO., LTD., the same applies hereinafter), and then 200 g of ion exchanged water was added for filtration washing. A cake of fumaric acid after the filtration was dried at 105° C. to obtain fumaric acid. To 0.2 g of the dried fumaric acid, 4 mL of 1 mol/L NaOH was added to dissolve the fumaric acid, however, the fumaric acid was not dissolved completely and yellow turbid liquid was obtained. The absorbance of the liquid at a wavelength of 400 nm was 2.0.

Comparative Example 4

Crystallization of fumaric acid was carried out in a jacket reactor (diameter of the reactor: 7.5 cm) having an internal volume of 600 mL equipped with an anchor blade having a blade diameter of 7 cm with stirring speed of 200 r/min.

First, 450 g of the culture medium obtained in Example 1(1) described above was heated to 60° C. Then, 0.45 g of hexadecyltrimethylammonium bromide was added, and then sulfuric acid was added to adjust the pH to 2.2. Then, the culture medium was cooled to 5° C. at a cooling rate of 0.6° C./min to crystallize fumaric acid. Then the fumaric acid suspension in which fumaric acid was crystallized was filtered with suction using a No. 2 filter paper (MANUFACTURED BY ADVANTECH CO., LTD., the same applies hereinafter), and then 200 g of ion exchanged water was added for filtration washing. A cake of fumaric acid after the filtration was dried at 105° C. to obtain fumaric acid. The absorbance of the purified fumaric acid at 400 nm was 0.044.

TABLE 1

| (g) | | Example 1 | Example 2 | Example 3 | Example 4 | Example 5 | Example 6 | Example 7 |
|---|---|---|---|---|---|---|---|---|
| Culture medium | | 450 | 450 | 450 | 450 | 450 | 450 | 450 |
| 47% Sulfuric acid | | 13 | 13 | 13 | 13 | 13 | 13 | 13 |
| Polyoxyethylene (6) lauryl ether | EMULGEN 108 | 0.45 | — | — | — | — | — | — |
| Polyoxyethylene (12) lauryl ether | EMULGEN 120 | — | 0.45 | — | — | — | — | — |
| Polyoxyethylene (47) lauryl ether | EMULGEN 150 | — | — | 0.45 | — | — | — | — |
| Polyoxyethylene (20) sorbitan monolaurate | — | — | — | — | 0.45 | — | — | — |
| Polyoxyethylene (20) sorbitan monooleate | — | — | — | — | — | 0.45 | — | — |
| Polyoxyethylene polyoxypropylene (C12-C14) alkyl ether | EMULGEN LS-114 | — | — | — | — | — | — | 0.45 | — |
| Polyoxyethylene (60) hydrogenated castor oil | EMANON CH-60(K) | — | — | — | — | — | — | 0.45 |
| Polyoxyethylene (60) sorbitol tetraoleate | RHEODOL 460V | — | — | — | — | — | — | — |
| Polyoxyethylene (12) lauryl ether | EMULGEN 120 | — | — | — | — | — | — | — |
| Polyoxyethylene (12) lauryl ether | EMULGEN 120 | — | — | — | — | — | — | — |
| Polyoxyethylene (12) lauryl ether | EMULGEN 120 | — | — | — | — | — | — | — |
| Polyoxyethylene (12) lauryl ether | EMULGEN 120 | — | — | — | — | — | — | — |
| Polyoxyethylene (12) lauryl ether | EMULGEN 120 | — | — | — | — | — | — | — |
| Polyoxyethylene (12) lauryl ether | EMULGEN 120 | — | — | — | — | — | — | — |

TABLE 1-continued

| | | | | | | | | |
|---|---|---|---|---|---|---|---|---|
| Lauryldimethylamino acetic acid betaine | AMPHITOL 20BS | — | — | — | — | — | — | — |
| 3-[(3-Cholamidopropyl)dimethylammonio]-1-propanesulfonate | CHAPS | — | — | — | — | — | — | — |
| Sodium lauryl sulfate | EMAL 0 | — | — | — | — | — | — | — |
| Hexadecyltrimethylammonium bromide | — | — | — | — | — | — | — | — |
| Stirring speed [r/min] | | 200 | 200 | 200 | 200 | 200 | 200 | 200 |
| Temperature of heating [° C.] | | 60 | 60 | 60 | 60 | 60 | 60 | 60 |
| pH | | 2.2 | 2.1 | 2.1 | 2.3 | 2.3 | 2.4 | 2.4 |
| Cooling rate [° C./min] | | 0.6 | 0.6 | 0.6 | 0.6 | 0.6 | 0.6 | 0.6 |
| Temperature of cooling [° C.] | | 5 | 5 | 5 | 5 | 5 | 20 | 21 |
| Temperature of drying [° C.] | | 105 | 105 | 105 | 105 | 105 | 105 | 105 |
| Absorbance of fumaric acid | | 0.015 | 0.009 | 0.012 | 0.016 | 0.012 | 0.015 | 0.016 |

| (g) | | Example 8 | Example 9 | Example 10 | Example 11 | Example 12 | Example 13 | Example 14 |
|---|---|---|---|---|---|---|---|---|
| Culture medium | | 450 | 450 | 450 | 450 | 450 | 450 | 459 |
| 47% Sulfuric acid | | 27 | 13 | 13 | 13 | 13 | 13 | 27 |
| Polyoxyethylene (6) lauryl ether | EMULGEN 108 | — | — | — | — | — | — | — |
| Polyoxyethylene (12) lauryl ether | EMULGEN 120 | — | — | — | — | — | — | — |
| Polyoxyethylene (47) lauryl ether | EMULGEN 150 | — | — | — | — | — | — | — |
| Polyoxyethylene (20) sorbitan monolaurate | | — | — | — | — | — | — | — |
| Polyoxyethylene (20) sorbitan monooleate | | — | — | — | — | — | — | — |
| Polyoxyethylene polyoxypropylene (C12-C14) alkyl ether | EMULGEN LS-114 | — | — | — | — | — | — | — |
| Polyoxyethylene (60) hydrogenated castor oil | EMANON CH-60(K) | — | — | — | — | — | — | — |
| Polyoxyethylene (60) sorbitol tetraoleate | RHEODOL 460V | 0.45 | — | — | — | — | — | — |
| Polyoxyethylene (12) lauryl ether | EMULGEN 120 | — | 0.0045 | — | — | — | — | — |
| Polyoxyethylene (12) lauryl ether | EMULGEN 120 | — | — | 0.045 | — | — | — | — |
| Polyoxyethylene (12) lauryl ether | EMULGEN 120 | — | — | — | 4.5 | — | — | — |
| Polyoxyethylene (12) lauryl ether | EMULGEN 120 | — | — | — | — | 0.45 | — | — |
| Polyoxyethylene (12) lauryl ether | EMULGEN 120 | — | — | — | — | — | 0.45 | — |
| Polyoxyethylene (12) lauryl ether | EMULGEN 120 | — | — | — | — | — | — | 0.45 |
| Lauryldimethylamino acetic acid betaine | AMPHITOL 20BS | — | — | — | — | — | — | — |
| 3-[(3-Cholamidopropyl)dimethylammonio]-1-propanesulfonate | CHAPS | — | — | — | — | — | — | — |
| Sodium lauryl sulfate | EMAL 0 | — | — | — | — | — | — | — |
| Hexadecyltrimethylammonium bromide | — | — | — | — | — | — | — | — |
| Stirring speed [r/min] | | 200 | 200 | 200 | 200 | 200 | 200 | 300 |
| Temperature of heating [° C.] | | 60 | 60 | 60 | 60 | 60 | 60 | 60 |
| pH | | 1.0 | 2.3 | 2.3 | 2.2 | 2.3 | 2.1 | 1.0 |
| Cooling rate [° C./min] | | 0.6 | 0.6 | 0.6 | 0.6 | 0.1 | 5 | 0.6 |
| Temperature of cooling [° C.] | | 20 | 5 | 5 | 5 | 21 | 10 | 20 |
| Temperature of drying [° C.] | | 105 | 105 | 105 | 105 | 105 | 105 | 105 |
| Absorbance of fumaric acid | | 0.015 | 0.018 | 0.010 | 0.004 | 0.016 | 0.017 | 0.008 |

| (g) | | Example 15 | Example 16 | Example 17 | Comparative Example 1 | Comparative Example 3 | Comparative Example 4 |
|---|---|---|---|---|---|---|---|
| Culture medium | | 450 | 450 | 450 | 450 | 450 | 450 |
| 47% Sulfuric acid | | 10 | 13 | 13 | 13 | 13 | 13 |
| Polyoxyethylene (6) lauryl ether | EMULGEN 108 | — | — | — | — | — | — |
| Polyoxyethylene (12) lauryl ether | EMULGEN 120 | — | — | — | — | — | — |
| Polyoxyethylene (47) lauryl ether | EMULGEN 150 | — | — | — | — | — | — |
| Polyoxyethylene (20) sorbitan monolaurate | | — | — | — | — | — | — |
| Polyoxyethylene (20) sorbitan monooleate | | — | — | — | — | — | — |
| Polyoxyethylene polyoxypropylene (C12-C14) alkyl ether | EMULGEN LS-114 | — | — | — | — | — | — |
| Polyoxyethylene (60) hydrogenated castor oil | EMANON CH-60(K) | — | — | — | — | — | — |
| Polyoxyethylene (60) sorbitol tetraoleate | RHEODOL 460V | — | — | — | — | — | — |
| Polyoxyethylene (12) lauryl ether | EMULGEN 120 | — | — | — | — | — | — |
| Polyoxyethylene (12) lauryl ether | EMULGEN 120 | — | — | — | — | — | — |
| Polyoxyethylene (12) lauryl ether | EMULGEN 120 | — | — | — | — | — | — |
| Polyoxyethylene (12) lauryl ether | EMULGEN 120 | — | — | — | — | — | — |
| Polyoxyethylene (12) lauryl ether | EMULGEN 120 | — | — | — | — | — | — |
| Polyoxyethylene (12) lauryl ether | EMULGEN 120 | 0.45 | — | — | — | — | — |
| Lauryldimethylamino acetic acid betaine | AMPHITOL 20BS | — | 0.45 | — | — | — | — |
| 3-[(3-Cholamidopropyl)dimethylammonio]-1-propanesulfonate | CHAPS | — | — | 0.45 | — | — | — |
| Sodium lauryl sulfate | EMAL 0 | — | — | — | — | 0.45 | — |
| Hexadecyltrimethylammonium bromide | — | — | — | — | — | — | 0.45 |

TABLE 1-continued

| | | | | | | |
|---|---|---|---|---|---|---|
| Stirring speed [r/min] | 100 | 200 | 200 | 200 | 200 | 200 |
| Temperature of heating [° C.] | 60 | 60 | 60 | 60 | 60 | 60 |
| pH | 3.2 | 2.1 | 2.3 | 2.0 | 2.1 | 2.2 |
| Cooling rate [° C./min] | 0.5 | 0.6 | 0.6 | 0.6 | 0.6 | 0.6 |
| Temperature of cooling [° C.] | 4 | 5 | 5 | 5 | 5 | 5 |
| Temperature of drying [° C.] | 105 | 105 | 105 | 105 | 105 | 105 |
| Absorbance of fumaric acid | 0.019 | 0.016 | 0.017 | 0.026 | 2.000 | 0.044 |

Example 19

(1) Obtaining Culture Medium

A culture medium was obtained by culturing *Rhizopus* sp. in a manner similar to that of Example 1.

(2) Crystallization of Fumaric Acid

Crystallization of fumaric acid was carried out in a jacket reactor (diameter of the reactor: 7.5 cm) having an internal volume of 600 mL equipped with an anchor blade having a blade diameter of 7 cm with stirring speed of 200 r/min in a manner similar to that of Example 1.

First, to 450 g of the culture medium obtained in (1) described above, 0.45 g of EMULGEN 120 was added, and then cooled to 5° C. Then, fumaric acid was crystallized by adding sulfuric acid at an addition rate of 0.5 [mmol $H_2SO_4$/L of culture medium/min] to make the pH 2.3. Then the fumaric acid suspension in which fumaric acid was crystallized was filtered with suction using a No. 2 filter paper (MANUFACTURED BY ADVANTECH CO., LTD., the same applies hereinafter), and then 200 g of ion exchanged water was added for filtration washing. A cake of fumaric acid after the filtration was dried at 105° C. to obtain fumaric acid. The absorbance of the purified fumaric acid at 400 nm was 0.015.

Example 20

Fumaric acid was obtained in the same manner as Example 19, except that pH and acid addition rate were modified as shown in Table 2. Further, the absorbance of purified fumaric acid at 400 nm was also as shown in Table 2.

Comparative Example 5

Crystallization of fumaric acid was carried out in a jacket reactor (diameter of the reactor: 7.5 cm) having an internal volume of 600 mL equipped with an anchor blade having a blade diameter of 7 cm with stirring speed of 200 r/min in a manner similar to that of Example 1.

First, 450 g of the culture medium obtained in (1) described above was cooled to 5° C. Then, fumaric acid was crystallized by adding sulfuric acid at an addition rate of 5.5 [mmol $H_2SO_4$/L of culture medium/min] to make the pH 2.2. Then the fumaric acid suspension in which fumaric acid was crystallized was filtered with suction using a No. 2 filter paper (MANUFACTURED BY ADVANTECH CO., LTD., the same applies hereinafter), and then 200 g of ion exchanged water was added for filtration washing. A cake of fumaric acid after the filtration was dried at 105° C. to obtain fumaric acid. The absorbance of the purified fumaric acid at 400 nm was 0.041.

TABLE 2

| (g) | Example 19 | Example 20 | Comparative Example 5 |
|---|---|---|---|
| Culture medium | 450 | 450 | 450 |
| 47% Sulfuric acid | 13 | 13 | 13 |
| Polyoxyethylene EMULGEN (12) lauryl ether 120 | 0.45 | 0.45 | — |
| Stirring speed [r/min] | 200 | 200 | 200 |
| Temperature of cooling [° C.] | 5 | 5 | 5 |
| Rate of addition of sulfuric acid [mmol $H_2SO_4$/L of culture medium/min] | 0.5 | 2.7 | 5.5 |
| pH | 2.3 | 2.1 | 2.2 |
| Temperature of drying [° C.] | 105 | 105 | 105 |
| Absorbance of fumaric acid | 0.015 | 0.018 | 0.041 |

As shown in Table 1, the color of fumaric acid was sufficiently removed by a method of the present invention, and the purified fumaric acid had favorable tone of color. From Table 2, it was found that a lower acid addition rate in crystallization by pH control tended to result in favorable tone of color of fumaric acid.

Further, according to the method of the present invention, an effect of removing the color was achieved even when an amount of a surfactant used was small.

On the other hand, when fumaric acid was purified by an activated carbon treatment at an industrially applicable level before the crystallization step, coloration was not reduced sufficiently. Further, when an excess activated carbon was used, coloration of fumaric acid tended to be reduced, however, a fumaric acid recovery rate was considerably reduced by adsorption of fumaric acid onto the activated carbon (data not shown).

Thus, according to the method of the present invention, fumaric acid having favorable tone of color can be obtained without reduction of the recovery rate due to an adsorption treatment, for example, a conventional adsorption treatment with activated carbon.

The invention claimed is:

1. A method for manufacturing fumaric acid, comprising the following steps (1) and (2):
   (1) a step of culturing a microorganism having fumaric acid-producing ability in a liquid culture medium comprising a carbon source to obtain one or more substances selected from the group consisting of fumaric acid and a fumarate,
   (2) a step of crystallizing the one or more substances selected from the group consisting of fumaric acid and a fumarate obtained in the step (1) in the presence of one or more surfactants selected from the group consisting of a nonionic surfactant and an amphoteric surfactant.

2. The method for manufacturing fumaric acid according to claim 1, wherein the microorganism having fumaric acid-producing ability is *Rhizopus* sp.

3. The method for manufacturing fumaric acid according to claim 1, wherein the nonionic surfactant is a nonionic surfactant having HLB of 10 or more.

4. The method for manufacturing fumaric acid according to claim 3, wherein the nonionic surfactant having HLB of 10 or more is at least one surfactant selected from the group consisting of polyoxyethylene alkyl ether, polyoxyethylene sorbitan fatty acid ester, polyoxyethylene hydrogenated castor oil, polyoxyethylene sorbitol fatty acid ester, and polyoxyethylene polyoxypropylene alkyl ether.

5. The method for manufacturing fumaric acid according to claim 1, wherein a total concentration of surfactants in a culture medium or an aqueous solution comprising one or more substances selected from the group consisting of fumaric acid and a fumarate is from 0.0001 to 5% by mass.

6. The method for manufacturing fumaric acid according to claim 1, wherein the step (2) further comprises a step of adjusting a pH of the culture medium comprising one or more substances selected from the group consisting of fumaric acid and a fumarate obtained in the step (1) to 3.5 or less.

7. The method for manufacturing fumaric acid according to claim 1, wherein a method for crystallizing fumaric acid is one or more methods selected from the group consisting of crystallization by pH control, crystallization by cooling, and crystallization by concentration.

8. The method for manufacturing fumaric acid according to claim 7, wherein a rate of addition of an acid used for the crystallization by pH control is from 0.1 [mmol acid/L of culture medium/min] to 20 [mmol acid/L of culture medium/min].

9. The method for manufacturing fumaric acid according to claim 7, wherein a cooling rate of the crystallization by cooling is from 0.05 (° C./min) to 10 (° C./min).

10. The method for manufacturing fumaric acid according to claim 1, further comprising (1-A) a step between the step (1) and the step (2), the step (1-A) of adding one or more surfactants selected from the group consisting of a nonionic surfactant and an amphoteric surfactant to the culture medium or the aqueous solution containing the one or more substances selected from the group consisting of fumaric acid and a fumarate obtained in the step (1).

11. A method for manufacturing fumaric acid, comprising the following steps (1) and (2):
(1) a step of culturing a microorganism having fumaric acid-producing ability in a liquid medium comprising a carbon source to obtain one or more substances selected from the group consisting of fumaric acid and a fumarate,
(2) a step of crystallizing the one or more substances selected from the group consisting of fumaric acid and a fumarate obtained in the step (1) in the presence of one or more surfactants selected from the group consisting of a nonionic surfactant and an amphoteric surfactant;
wherein the method further comprises adding one or more surfactants selected from the group consisting of a nonionic surfactant and an amphoteric surfactant after the step (1).

12. The method for manufacturing fumaric acid according to claim 1, wherein an amount of the surfactant used in crystallization of fumaric acid is 0.0001 or more and 1 or less relative to the one or more substances selected from the group consisting of fumaric acid and a fumarate.

13. The method for manufacturing fumaric acid according to claim 1, wherein the total concentration of the surfactants in crystallization of fumaric acid is 0.0001% by mass or more and 5% by mass or less in the culture medium or the aqueous solution containing the one or more substances selected from the group consisting of fumaric acid and a fumarate.

* * * * *